United States Patent
Sisson

[19]

[11] Patent Number: 5,968,003
[45] Date of Patent: Oct. 19, 1999

[54] COMPRESSION BANDAGE

[75] Inventor: Suzanne L. Sisson, Palatine, Ill.

[73] Assignee: Isaacs-Sisson Enterprises, Ltd., Palatine, Ill.

[21] Appl. No.: 08/509,786

[22] Filed: Aug. 1, 1995

[51] Int. Cl.⁶ .................................................... A61F 5/00
[52] U.S. Cl. ................................ 602/75; 602/19; 602/53
[58] Field of Search .................................. 602/41, 75, 79, 602/42, 76, 19, 53; 2/308, 309, 310, 311; 450/1, 12–132, 155

[56] References Cited

U.S. PATENT DOCUMENTS

| | | |
|---|---|---|
| 643,911 | 2/1900 | Sahlin . |
| 1,115,674 | 11/1914 | Jacob . |
| 2,052,412 | 8/1936 | Lichtensteiger . |
| 3,189,028 | 6/1965 | Dormire . |
| 3,442,270 | 5/1969 | Steinman . |
| 3,561,442 | 2/1971 | Goswitz ..................................... 602/41 |
| 3,968,803 | 7/1976 | Hyman . |
| 4,665,909 | 5/1987 | Trainor ..................................... 602/76 |
| 4,781,651 | 11/1988 | Ekins . |
| 4,957,466 | 9/1990 | Hopps . |
| 5,060,648 | 10/1991 | Zarkesh . |
| 5,098,331 | 3/1992 | Corrado . |
| 5,148,549 | 9/1992 | Sydor ....................................... 602/19 |
| 5,152,741 | 10/1992 | Farnio . |
| 5,158,541 | 10/1992 | McCurley ................................. 602/79 |
| 5,205,815 | 4/1993 | Saunders ................................... 602/19 |
| 5,499,965 | 3/1996 | Sanchez .................................... 602/19 |

FOREIGN PATENT DOCUMENTS

| | | | |
|---|---|---|---|
| 721902 | 3/1932 | France ..................................... 602/79 |
| 2279344 | 2/1976 | France ..................................... 602/79 |

*Primary Examiner*—Richard J. Apley
*Assistant Examiner*—Kim M. Lee
*Attorney, Agent, or Firm*—Olson & Hierl, Ltd.

[57] ABSTRACT

A compression bandage according to the present invention includes an expandable band that overlaps a post-operative breast to support and provide secondary compression, and compression flaps each having first and second ends, the first ends being connected to the expandable band adjacent the area to be compressed and the second ends being securable. The compression flaps compress the post-operative breast when longitudinally extended, and maintain the compression when the second ends are fastened. The compression bandage further comprises at least one shoulder support or strap connected to the expandable band to reduce movement of the bandage. The compression bandage can also have an support belt attached to the expandable band for supporting the area to be compressed.

15 Claims, 4 Drawing Sheets

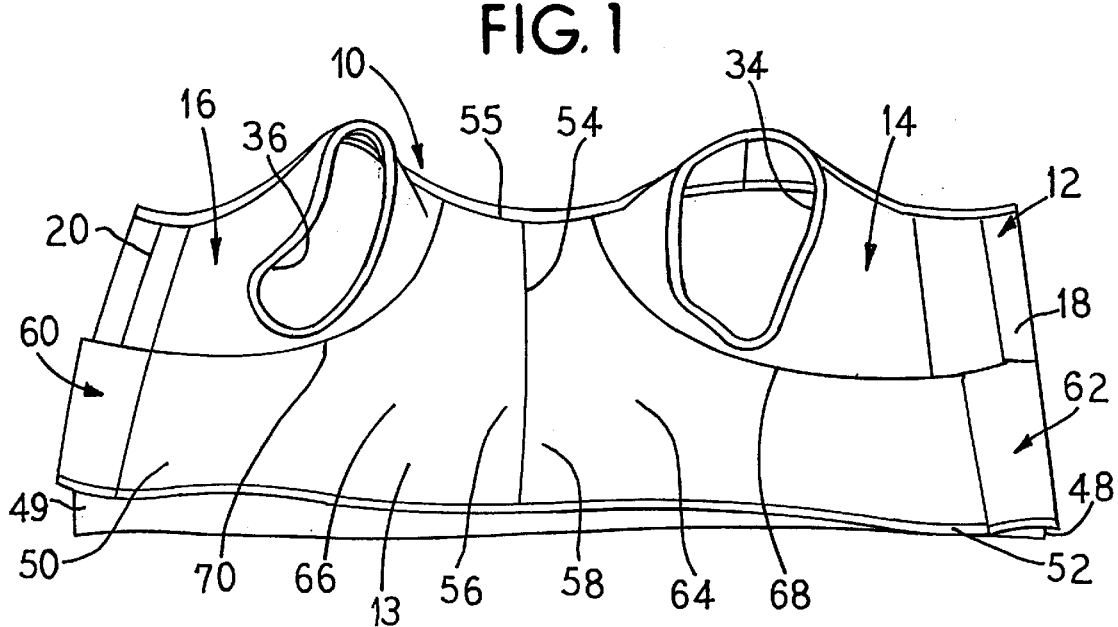
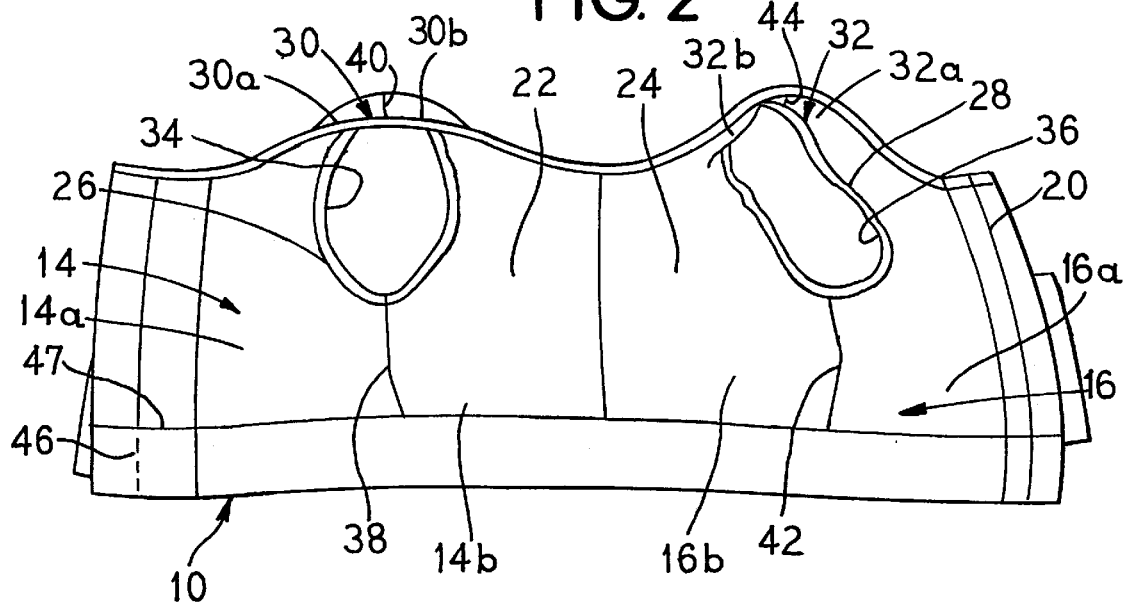

COMPRESSION BANDAGE

FIELD OF THE INVENTION

The present invention relates to a medical bandage for a breast. More particularly, the present invention relates to a compression bandage for preventing complications in a post-operative breast.

BACKGROUND OF THE INVENTION

It was projected that in 1994 there would be about 182,000 newly diagnosed breast cancer patients in the United States alone. It was estimated that between 4 to 10 percent of those patients needed biopsies to establish these diagnoses. Although the complication rate is about 5–10 percent, this still represents a sizeable number and thus must be addressed.

Complications arising from breast biopsies include infections, pain, ecchymoses and hematomas. Infection and pain can be effectively prevented or treated with medication. Ecchymosis and a hematoma, however, are not as effectively treated by medication.

During a biopsy, an incision is made in or around the breast. The targeted tissue is then partially or entirely removed for examination. During the removal process, a cavity is formed where the tissue was removed, and blood vessels may be incised that will cause internal bleeding (ecchymosis), possibly filling the cavity (hematoma).

A serious problem caused by ecchymosis or a hematoma is that malignant cells can be disseminated along the planes where ecchymosis or a hematoma exists, thus decreasing the probability of local control. This is in addition to the pain, tenderness and skin discoloration caused by these complications that detract from a patient's sense of well-being.

It has been reported that breast support is necessary during the immediate post-operative period to help prevent ecchymosis and hematoma. Also, compression has been used to reducing scarring from severe burns. Thus, compression could minimize scarring of the biopsy site. To this end, an ace bandage has been tightly wrapped around the chest to compress a post-operative breast. The compression closes the cavity and compresses the incised blood vessel to prevent and eventually terminate bleeding.

To apply the ace bandage wrap, the patient's torso must be positioned for facilitated circumnavigation of the chest, typically in a somewhat upright position. But the design of the ace bandage lends itself to awkward application, which is further exacerbated when the patient has been subjected to general anesthesia. Also, the ace bandage is hot, uncomfortable and is not easy to adjust its compression or fit once on the patient.

A surgical chest dressing is disclosed in U.S. Pat. No. 5,152,741 to Farnio entitled "SURGICAL CHEST DRESSING." It is formed from a chest encircling band of stretchable material with free ends that engage each other between the breasts. The band is constructed so as to provide more support along the sides of the user's body as compared with the support generally provided for the breasts and the back of the patient.

The dressing disclosed in the Farnio patent is not suitable for effective hematoma or ecchymosis prevention. The Farnio patent discloses that the dressing will conform to the body upon application and exert very little force on the patient. Specifically, front flaps of the disclosed dressing are made of a material that conforms to the shape that it overlays without exerting substantial pressure. The Farnio patent further discloses the desirability of material that will stretch out and accommodate different sized breasts. Thus, the dressing disclosed in the Farnio Patent is less effective at preventing a hematoma or ecchymosis than the ace bandage since its material conforms to, but does not exert a pronounced pressure on the breast.

U.S. Pat. No. 4,781,651 to Ekins entitled "ATHLETIC SUPPORT BRASSIERE" discloses a brassiere for energetic activities including an encircling band that has stretchable and elastic portions. Attached to the band are two cups that include relatively inelastic, non-stretchable material. A stabilizer strip is located directly beneath the encircling band to support the breasts by preventing their downward sag.

The brassiere disclosed in the Ekins patent also does not provide the requisite compression to effectively prevent a hematoma or ecchymosis. First, by the very nature of the cups of the disclosed brassiere, the breast is not compressed, but is shaped. Second, the material used for the cups is relatively inelastic and non-stretchable which also does not effectively compress the breast. Finally, the stabilizing strip simply prevents the breast from downward sag. This in no way compresses the breast to prevent a hematoma or ecchymosis.

Another chest dressing is disclosed in U.S. Pat. No. 5,098,331 to Corrado entitled "THERAPEUTIC CHEST DRESSING FOR BREASTS HAVING IMPLANTS." The dressing disclosed includes a chest encircling, flexible band provided with front flaps that engage each other while overlaying the breasts. A chest encircling strip is attached to the flexible band for preventing movement or distortion of the breast implants received in the flexible band.

The dressing disclosed in the patent to Corrado will not provide effective prevention of a hematoma or ecchymosis for many reasons. Most importantly, the Corrado dressing is designed not to compress the breast since that would be detrimental to the implant's shape and location in the chest. Specifically, most breast implants are located between the pectoralis major and minor muscles. Some body movement will cause the implants to rise between these muscles, which is not desired. Compressing the implants will also cause them to move intermuscularly with the additional side effect of misshaping the implants. Thus, compression is not desired for the disclosed dressing.

In addition, the Corrado dressing only applies minimal pressure to the upper surface of the breast. This in no way will provide the requisite compression needed to effectively prevent a hematoma or ecchymosis; it simply prevents intermuscular movement of the implants.

Thus, there still exists a need for a bandage that compresses a post-operative breast to effectively prevent hematoma or ecchymosis, and that is easy to apply, easily adjustable to fit, economical and comfortable. The present invention meets this need.

SUMMARY OF THE INVENTION

A compression bandage according to the present invention includes an expandable band that overlays an area, such as a post-operative breast, to support and provide secondary compression. Compression flaps are connected to the expandable band adjacent the area to be compressed at first ends and are fastenable together at second ends. The compression flaps compress the post-operative breast when longitudinally extended, and maintain the compression when the second ends are fastened together. The compression flaps can define contoured edges that allow for a comfortable fit under the shoulder of the patient while maximizing the area for effective compression of the postoperative breast.

The compression bandage preferably also includes at least one shoulder support or strap connected to the expandable band to reduce movement of the bandage. A support belt can be attached to the expandable band for supporting the area to be compressed, preventing movement of the compression bandage and for additional comfort.

One of the numerous advantages of the preferred embodiment of the present invention is that effective compression of the breast is provided by applying compression via the flaps. This compression is augmented by having first ends of the flaps connected to a portion of the band that is adjacent to the breast, preferably over the sternum. The flaps and a VELCRO fastener attached to second ends of the flaps allow for easy and quick application and adjustment of the compression. Further, the configuration of the components of the preferred embodiment facilitates manufacturing the bandage and provides increased user comfort.

Another advantage of the present invention is that the compression bandage can be configured so that the patient cannot remove the bandage after it is applied. To this end, the ends of the band and compression flaps, if either is provided with ends, are preferably secured at the back of the patient. In this manner, the patient cannot easily reach and detach the ends to remove the bandage. This bandage configuration lends itself toward applications for specific uninterrupted time durations while deterring patient removal.

Numerous other advantages and features of the present invention will become readily apparent from the following detailed description of the invention and the embodiments thereof, from the claims and from the accompanying drawings in which details of the invention are fully and completely disclosed as a part of this specification.

BRIEF DESCRIPTION OF THE DRAWINGS

In the drawings,

FIG. 1 is a plan view of the outer side of a compression bandage in an open condition that embodies the present invention;

FIG. 2 is a plan view of the inner side of the FIG. 1 embodiment in an open condition;

DETAILED DESCRIPTION OF THE PREFERRED EMBODIMENTS

Figure 3:
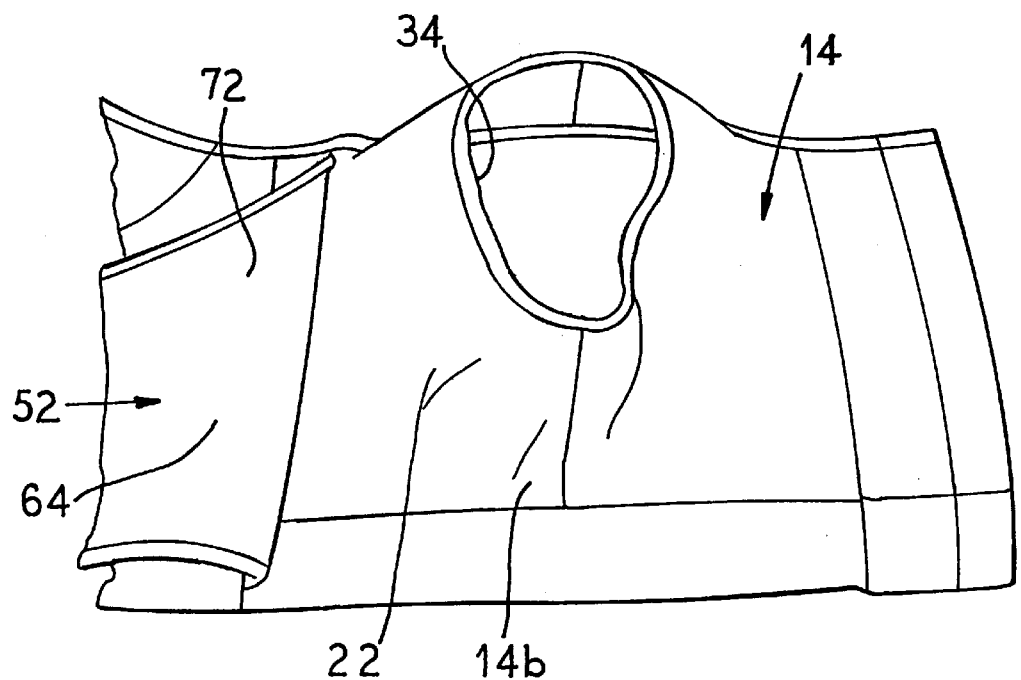
FIG. 3 is a side view of the FIG. 1 embodiment in an open condition.

While this invention is susceptible of embodiment in many different forms, there are shown in the drawings and will be described herein in detail specific embodiments thereof with the understanding that the present disclosure is to be considered as an exemplification of the principles of the invention and is not to be limited to the specific embodiments illustrated.

Shown in FIG. 1 is the outer side of a compression bandage 10 that includes an expandable band 12 and a butterfly 13. Expandable band 12 has side portions 14 and 16 connected together, and terminates at a first end 18 and a second end 20. Preferably, VELCRO hooks are attached to first end 18 to detachably engage VELCRO strands attached to second end 20 (shown in FIG. 2), the strands and hooks being complimentary members of a fastener. Alternatively, other fasteners such as snaps, buttons, zippers, ties and the like can be used.

As the inner side of the compression bandage 10 is illustrated in FIG. 2, expandable band 12 also includes breast regions 22 and 24 that preferably envelope and support a respective breast when disposed therein. Adjacent these regions are shoulder boundaries 26 and 28 of respective side portions 14 and 16.

Shoulder straps 30 and 32 are attached to expandable band 12 at side portions 14 and 16, respectively. It is preferred that shoulder straps are integral with expandable band 12. However, shoulder straps 30 and 32 may be physically separate and attached, either removably or permanently, to expandable band 12.

It is also preferred that side portions 14 and 16 include panels 14a and 14b, and 16a and 16b, respectively, as shown in FIG. 2. Panels 14a, 14b, 16a and 16b respectively include shoulder strap segments 30a, 30b, 32a and 32b. Panels 14a and 14b are connected at seams 38 and 40, and panels 16a and 16b are connected at seams 42 and 44. Alternatively, expandable band 12 can have a unitary construction to provide more uniform compression of the breasts and chest.

The shoulder boundaries 26 and 28, and the shoulder straps 30 and 32 define respective shoulder apertures 34 and 36. The use of panels 14a, 14b, 16a and 16b allows extra material in shoulder straps 30 and 32 to comfortably conform to a patient's shoulders that are placed in shoulder apertures 34 and 36 (see FIG. 4).

Additionally, it is preferred that shoulder boundaries 26 and 28, and the longitudinal edges of shoulder straps 30 and 32 that are adjacent the shoulder apertures 34 and 36 be rolled for comfort.

Expandable band 12 can also include a support belt 46, preferably elastic, attached at edge 47 of expandable band 12. Alternatively, support belt 46 may be integral with expandable band 12. Belt ends 48 and 49 (see FIG. 1) of support belt 46 preferably have attached VELCRO hooks and strands for detachable engagement together.

Material for expandable band 12 has can have either elastic or stretchable characteristics, with the difference between the two known in the art. The material can be chosen for specific properties, such as providing breathability to reduce heat build-up, elasticity, stretchability, weave and the desired amount of compression or support. Such material can be LYCRA, NYLON, SPANDEX, cotton blends or the like.

Returning to FIG. 1, butterfly 13 is preferably a one-piece elastic material that includes compression flaps 50 and 52. Butterfly 13 is attached to expandable band 12 at seams 54 and 55. Compression flaps 50 and 52 include respective first ends 56 and 58, and terminate in respective second ends 60 and 62. Preferably attached to end 60 is VELCRO strands that detachably engage VELCRO hooks attached to end 62, the hooks and strands forming a fastener. Other fasteners can be used as alternatives, such as the fasteners previously discussed. Flaps 50 and 52 include compression regions 64 and 66 that preferably envelope and compress a breast located immediately underneath. It is preferred to envelope the breast to provide compression over the entire breast, which aids in effectively lessening the occurrence of or preventing ecchymosis or hematoma.

Flaps 50 and 52 define contoured edges 68 and 70 to avoid obstructing the entrance of a patient's shoulders into shoulder apertures 34 and 36. Further, contoured edges 68 and 70 do not bind the patient's shoulders once located within shoulder apertures 34 and 36. The contoured edges 68 and 70 also allow more material to be used at first ends 56 and 58 to provide more effective compression over the entire breast.

To illustrate, FIG. 3 shows side portion 14 with compression flap 52 pulled away to expose breast region 22 of panel 14b. A rectangular shape for compression flap 52 that would allow unobstructed entrance into shoulder aperture 34 will necessarily eliminate a section 72 of compression region 64 from the compression flap 52. As a consequence, compression region 64, and hence the effective area of compression flap 52, would be reduced. The effective area is the area of a compression flap that effectively compresses a breast, in this instance it is compression region 64.

A larger rectangular shape of compression flap 52 that would obstruct shoulder aperture 34 will increase the area of compression region 64 greater than that shown in FIG. 3. However, this shape or configuration would bind the patient's shoulder in shoulder aperture 34 to cause discomfort. Therefore, preferred contoured edge 68 provides compression flap 52 with both maximized effective compression area and comfort. The same is true for preferred contoured edge 70 and compression flap 54.

Figure 4:
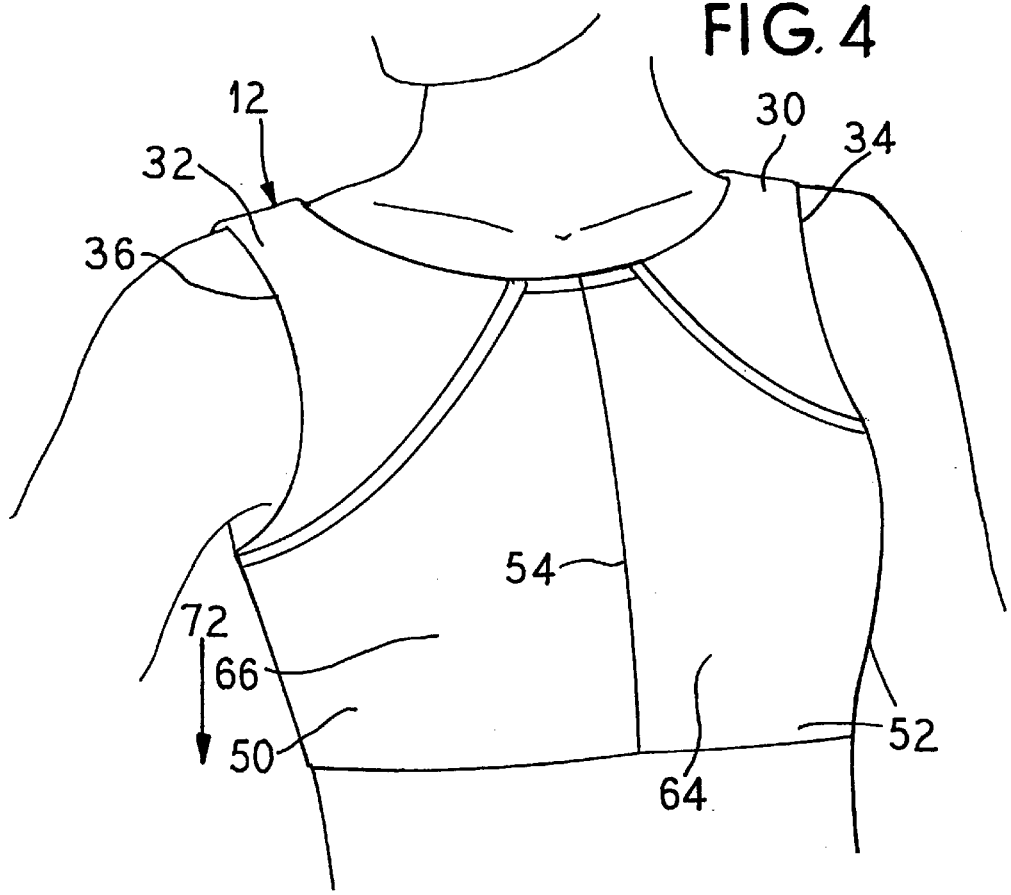
FIG. 4 is a perspective view of the FIG. 1 embodiment in a used and closed condition.

One use of the present invention can be seen in FIG. 4. A patient places her shoulders through shoulder apertures 34 and 36 of expandable band 12. Shoulder straps 30 and 32 rest on the shoulders to support and prevent compression bandage 10 from downward movement shown by arrow 72. The breast regions 22 and 24 of expandable band 12 (not shown) and the compression regions 64 and 66 of compression flaps 50 and 52 envelope the patient's breasts.

The first and second ends 18 and 20 of expandable band 12 are engaged together (shown in FIG. 5), and the second ends 60 and 62 of compression flaps 50 and 54 are engaged together (shown in FIG. 6) to maintain the compression of the patient's breasts as shown in FIG. 4. Engagement of the ends is accomplished by exerting longitudinal force from the seam 54.

Figure 5:
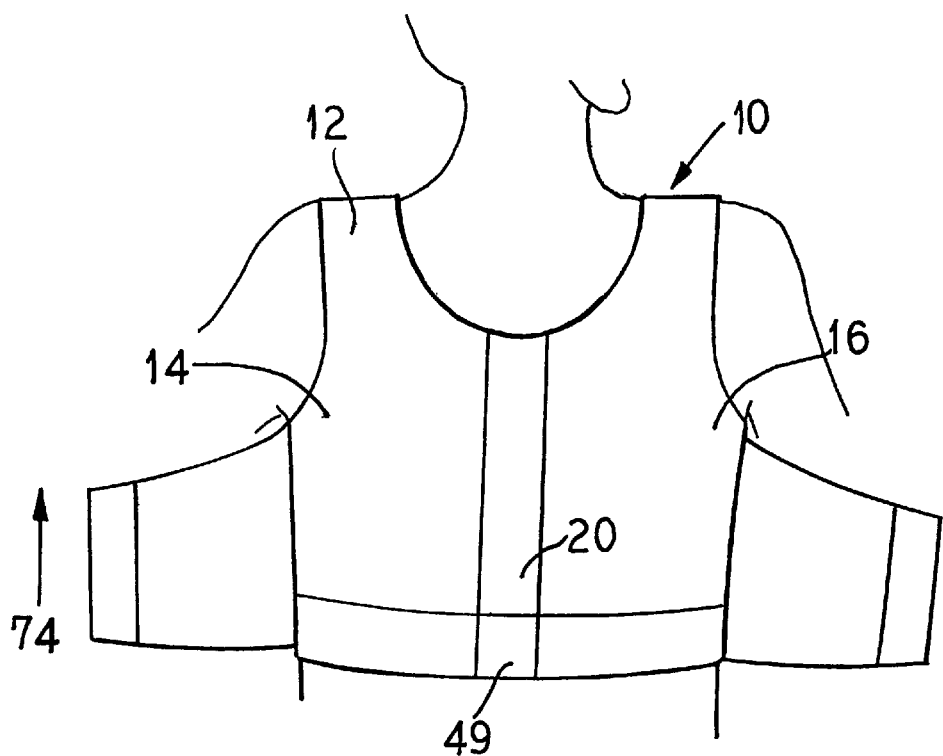
FIG. 5 is a rear view of the outer side of the FIG. 1 embodiment in a used and semi-closed condition.

FIG. 5 illustrates the engagement of first and second ends 18 and 20 of expandable band 12. Side portion 14 is longitudinally extended by a force until the corresponding breast is supported and, if desired, compressed. The first end 18 and belt end 48 (not shown) are preferably located proximate to the center of the patient's back.

A longitudinal force is exerted on side portion 16 to support and, if desired, compress the corresponding breast. Second end 20 and belt end 49 preferably then overlap and engage first end 18 and belt end 48, respectively, to at least maintain compression bandage 12 encircling the patient. More importantly, the engaged ends can maintain the support and, if desired, provide secondary compression of the patient's breasts by the expandable band 12. The closed support belt 46 helps prevent compression bandage 10 from upward movement as shown by arrow 74 while making compression bandage 10 more comfortable to wear.

Figure 6:
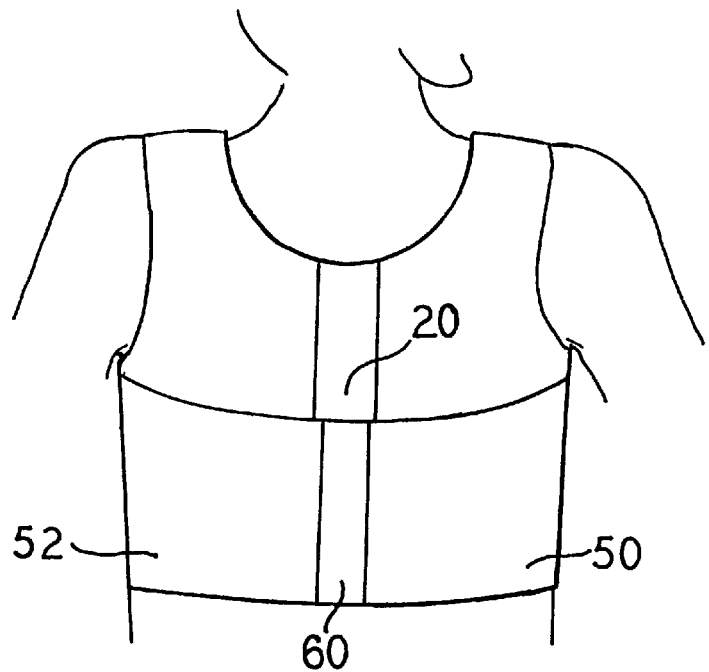
FIG. 6 is a view of the outer side of the FIG. 1 embodiment in a used and closed condition.

With reference to FIG. 6, a longitudinal force is exerted on compression flap 52 to compress the breast under compression region 64.

Second end 62 (not shown) then is preferably located adjacent second end 20 and belt end 48 (not shown). A longitudinal force is exerted on compression flap 50 to compress the breast under compression region 66. Second end 60 then preferably overlaps and engages second end 62 to maintain compression that effectively prevents hematoma or ecchymosis in either or both breasts.

Figure 7:
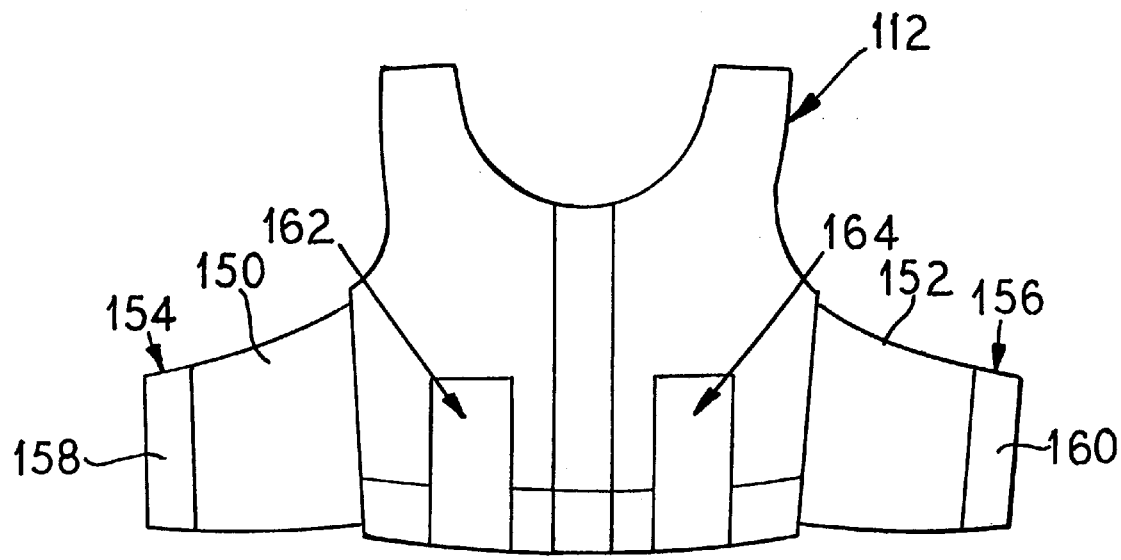
FIG. 7 is a rear view of the outer side of another embodiment in a semi-closed condition of the present invention.
Figure 8:
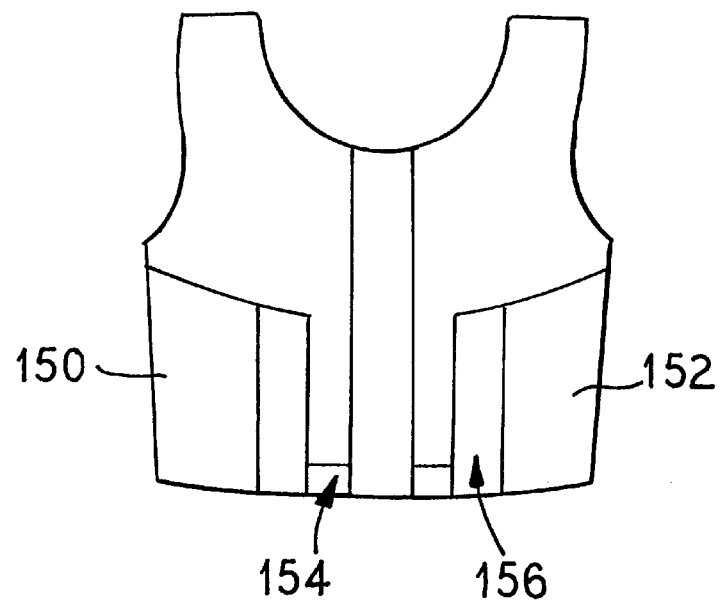
FIG. 8 is a rear view of the outer side of the FIG. 7 embodiment in a closed condition.

An alternative to the discussed engaging configuration of compression flaps 50 and 52 is shown in FIG. 7. Compression flaps 150 and 152 have respective ends 154 and 156. Each end has VELCRO hooks 158 and 160 attached. Attached to expandable band 112 are VELCRO strands 162 and 164. Longitudinal forces are exerted on compression flaps 150 and 152 to compress the breasts as desired. Ends 154 and 156 will preferably overlap VELCRO strands 162 and 164 so that VELCRO hooks 158 and 160 can engage VELCRO strands 162 and 164, respectively, as illustrated in FIG. 8 to maintain the compression of the breasts.

A benefit of using the VELCRO fasteners is that the compression bandage can be easily and comfortably adjusted for a satisfactory fit to the patient. A benefit to having the VELCRO fasteners in the rear of the compression bandage, or diametrically opposed to the area to be compressed, is that adjusting the bandage will not aggravate the already traumatized breast.

It is preferred that the compression bandage extend from the top of the sternum to the xiphoid process of the patient so that the compression bandage does not slide up on the patient's torso. It is also preferred that the ends of the band and the second ends of the flaps are located behind the patient at the rear of the bandage when secured so that the ends are hard to reach. This will deter the patient from removing the bandage since its removal is impeded by the placement of the ends behind and out of reach of the patient. Thus, the bandage can be used when it is necessary for the bandage to stay on the patient for an uninterrupted duration of time without the worry that the patient can easily remove it.

The present invention contemplates alternatives for the above-discussed components of the present invention. For example, metal fasteners can be used instead of VELCRO. Also, either or both expandable band 12 and butterfly 13 can be unitary and continuous. The compression bandage can be made of the same material or different materials.

Material for the present invention can have either elastic or stretchable characteristics. The material can be chosen for specific desired properties, such as providing breathability, elasticity, stretchability, the weave or the desired amount of compression or support, for example. Such material can be LYCRA, NYLON, SPANDEX, cotton blends or the like.

The present invention can be used for other applications. For instance, the compression bandage can be used by an athlete to prevent breast movement, thus providing support during physical activity. The compression bandage can also be used after lumpectomies, a stereostatic biopsy, or to prevent or control lactation post partum.

The preferred embodiment of the present invention can be modified according to its desired use. For example, if the bandage is used for post partum or sport applications, then providing a unitary band, i.e., having no ends, with the flaps having second ends is desirable. Depending on other desired applications, the band can have ends and the flaps can be without second ends, or the band can be without ends and the flaps can be without second ends.

What is claimed is:

1. A breast compression bandage comprising:

an expandable band adapted to receive and support the breasts of a wearer, the band having an inner surface and an outer surface, the band being of a size and shape to extend upwardly from a position immediately below the breasts and over the shoulders when worn, and defining shoulder apertures adapted to receive the shoulder of the wearer; and compression flaps attached to and substantially overlying the outer surface, the compression flaps each having first and second ends, the first ends being attached to the expandable band, the second ends being securable to each other behind the wear's back so as to receive, support and maintain compression of the wearer's breasts.

2. The compression bandage of claim 1 further comprising a support belt attached to the expandable band.

3. The compression bandage of claim 1 including a fastener having first and second complimentary members respectively located on the second ends of the flaps such that the complimentary members are detachably engageable.

4. The compression bandage of claim 1 wherein the expandable band is connected to the compression flaps, and the band includes at least one region that envelopes the area to be compressed and first and second ends that secure together to maintain the bandage in an encircling configuration.

5. The compression bandage of claim 1 wherein the compression flaps define contoured edges that maximize the effective compression area.

6. The compression bandage of claim 1 wherein the second ends of the compression flaps are securable together at a rear of the compression bandage.

7. The compression bandage of claim 1 wherein the second ends of the compression flaps are securable to the expandable band at a rear of the compression bandage.

8. The compression bandage of claim 1 wherein the expandable band includes panels.

9. The compression bandage of claim 1 wherein the expandable band and the shoulder straps are unitary.

10. The compression bandage of claim 1 wherein the expandable band and compression flaps are made of an elastic material.

11. The compression bandage of claim 1 wherein the expandable band and compression flaps are made of a stretchable material.

12. A post-surgery breast compression bandage, comprising:

a band including side portions connected together and terminating at first and second ends, the band adapted to receive, encompass, and support the post-surgery breast, the band forming shoulder straps and defining shoulder apertures adapted to receive the shoulders of a wearer; and a butterfly bandage overlaying the band and including compression flaps, the flaps having first ends connected to the band and second ends that are adjustably attachable to each other, whereby, during use worn, the first ends of the flaps are positioned between the wearer's breasts and a longitudinal force is exerted on the flaps such that the post-surgery breast is compressed and the compression is maintained by attaching the second ends together behind the wearer's back.

13. The breast compression bandage of claim 12 wherein the shoulder straps are integrated with the band.

14. The breast compression bandage of claim 12 wherein the flaps are contoured to provide unobstructed access to the shoulder apertures.

15. A method of compressing a post-surgery breast with a compression bandage having a plurality of flaps coupled to a band comprising the steps of:

securing the band around a torso and over the post-surgery breast to support the breast, the band being capable of compressing the breast and having an outer surface;

thereafter applying a longitudinal force to flaps that substantially overlay the outer surface about the post-surgery breast to compress the breast; and securing the flaps to maintain the compression of the breast.

* * * * *